(12) United States Patent  
Narendranath

(10) Patent No.: US 9,340,767 B2  
(45) Date of Patent: May 17, 2016

(54) PROPAGATING AN ORGANISM AND RELATED METHODS AND COMPOSITIONS

(71) Applicant: POET Research Inc., Sioux Falls, SD (US)

(72) Inventor: Neelakantam V. Narendranath, Sioux Falls, SD (US)

(73) Assignee: Poet Research, Inc., Sioux Falls, SD (US)

( * ) Notice: Subject to any disclaimer, the term of this patent is extended or adjusted under 35 U.S.C. 154(b) by 44 days.

(21) Appl. No.: 13/798,617

(22) Filed: Mar. 13, 2013

(65) Prior Publication Data

US 2014/0273166 A1 Sep. 18, 2014

(51) Int. Cl.  
*C12N 1/18* (2006.01)  
*C12N 1/16* (2006.01)

(52) U.S. Cl.  
CPC ... *C12N 1/18* (2013.01); *C12N 1/16* (2013.01)

(58) Field of Classification Search  
None  
See application file for complete search history.

(56) References Cited

U.S. PATENT DOCUMENTS

| | | | |
|---|---|---|---|
| 4,530,846 A | 7/1985 | Nagodawithana et al. | |
| 5,424,417 A | 6/1995 | Torget et al. | |
| 6,022,419 A | 2/2000 | Torget et al. | |
| 6,159,724 A | 12/2000 | Ehret | |
| 7,344,876 B2 | 3/2008 | Levine | |
| 7,622,284 B2 | 11/2009 | Op Den Camp et al. | |
| 7,820,418 B2 * | 10/2010 | Karl et al. | 435/161 |
| 7,968,320 B2 | 6/2011 | Degré et al. | |
| 8,105,801 B2 | 1/2012 | Nielsen et al. | |
| 8,450,094 B1 | 5/2013 | Narenadranath et al. | |
| 8,815,552 B2 | 8/2014 | Narendranath et al. | |
| 2004/0058429 A1 | 3/2004 | Bill et al. | |
| 2004/0234649 A1 | 11/2004 | Lewis et al. | |
| 2006/0051847 A1 | 3/2006 | Gunnarsson et al. | |
| 2006/0246563 A1 | 11/2006 | Eroma et al. | |
| 2009/0093027 A1 | 4/2009 | Balan et al. | |
| 2009/0325241 A1 | 12/2009 | Jeffries et al. | |
| 2010/0124759 A1* | 5/2010 | Wang et al. | 435/28 |
| 2010/0159552 A1 | 6/2010 | Benson et al. | |
| 2010/0196994 A1 | 8/2010 | van Leeuwen et al. | |
| 2010/0227369 A1 | 9/2010 | Narendranath et al. | |
| 2011/0262983 A1 | 10/2011 | Jeffries et al. | |
| 2011/0269202 A1 | 11/2011 | Taron et al. | |
| 2012/0309069 A1 | 12/2012 | Bell et al. | |
| 2014/0065700 A1 | 3/2014 | Narendranath et al. | |
| 2014/0273167 A1 | 9/2014 | Narendranath et al. | |

FOREIGN PATENT DOCUMENTS

| | | |
|---|---|---|
| WO | WO 2011/159915 | 12/2011 |
| WO | WO 2012/100187 | 7/2012 |
| WO | WO 2012/125739 | 9/2012 |

OTHER PUBLICATIONS

Kurth, "Yeasts from Wood Sugar Stillage" (1946), Industrial and Engineering Chemistry: vol. 38, No. 2: 204-207.*  
U.S. Appl. No. 14/465,177, filed Aug. 2014, Narendranath et al.  
Aiba, S. et al. "Fed Batch Culture of *Saccharomyces cerevisiae*; A Perspective of Computer Control to Enhance the Productivity in Baker's Yeast Cultivation", Biotechnology and Bioengineering XVIII (1976), pp. 1001-1016.  
Jeffries, T.W. et al. "Fermentation of Hemicellulosic Sugars and Sugar Mixtures by *Candida shehatae*", Biotechnology and Bioengineering 31 (1988), pp. 502-506.  
Soni S.K. et al. "A solid state fermentation based bacterial α-amylase and fungal glucoamylase system and its suitability for the hydrolysis of wheat starch", Process Biochemistry 39 (2003), pp. 185-192.

* cited by examiner

*Primary Examiner* — Robert Yamasaki  
*Assistant Examiner* — Teresa E Knight  
(74) *Attorney, Agent, or Firm* — Kagan Binder, PLLC

(57) ABSTRACT

The present invention is related to methods of propagating one or more organisms by using a carbon source that includes xylose (e.g., xylose syrup from pretreating lignocellulosic feedstock) and/or a nutrient source that includes a stillage component (e.g., thin stillage derived from a corn-to-ethanol process) in the propagation medium. The organisms include those that can convert one or more monosaccharides into an alcohol via fermentation, such as yeast. The present invention is also directed to related compositions.

18 Claims, 5 Drawing Sheets

|  | ETHANOL (% V/V) | |
|---|---|---|
| XYLOSE (% W/V) | YP MEDIA | THIN STILLAGE |
| 2.30 | 1.28 | 1.32 |
| 4.53 | 2.64 | 2.53 |
| 6.76 | 3.93 | 3.66 |
| 9.06 | 4.98 | 4.86 |
| 11.29 | 6.12 | 5.67 |
| 13.61 | 1.90 | 0.31 |
| 15.77 | ND | 0.00 |
| 17.61 | ND | NT |

ND - NOT DETECTED; NT - NOT TESTED.

Fig. 3A

| % THIN STILLAGE IN MAKEUP WATER | ETHANOL (% W/V) | RESIDUAL XYLOSE (% W/V) |
|---|---|---|
| 0 | 0 | 9.48 |
| 20 | 2.48 | 5.55 |
| 40 | 6.17 | 0.13 |
| 60 | 6.35 | 0.00 |
| 80 | 6.38 | 0.01 |

Fig. 4A

PROPAGATING AN ORGANISM AND RELATED METHODS AND COMPOSITIONS

FIELD OF INVENTION

The present invention relates to propagating one or more organisms that can convert one or more monosaccharides into an alcohol, such as ethanol, via fermentation.

BACKGROUND OF INVENTION

Organisms that can convert one or more monosaccharides into one or more biochemicals such as biofuels are well known. For example, both genetically modified (referred to as GM) yeast and non-genetically modified (referred to as non-GM) yeast are well known organisms that can convert sugars into alcohols such as ethanol and butanol via fermentation.

Often, such organisms are propagated by the manufacturer so as to produce a cell mass desired by a user, e.g., an ethanol manufacturer. However, many organisms are relatively quite expensive as compared to others. For example, many GM yeasts can be relatively much more expensive than non-GM yeasts. Thus, in some situations, it may be economically desirable for an ethanol manufacturer to purchase as little of a GM yeast as possible and then reproduce the yeast to provide a quantity sufficient for fermentation.

However, propagating yeast can be challenging. For example, some organisms such as *Saccharomyces cerevisiae* can be susceptible to the well-known "Crabtree effect" when grown on glucose, even under highly aerated conditions, if the glucose concentration in the medium is too high (e.g., exceeds 5 grams per Liter). If the glucose level becomes too high, the yeast can start to make ethanol through a fermentative pathway instead of producing more yeast through a respiration pathway (i.e., suppression of respiration by high levels of glucose). To help prevent the Crabtree effect, yeast manufacturers often grow yeast via a fed-batch or slow feeding process, where the carbon source (glucose) for producing yeast biomass is introduced at a rate that avoids undue ethanol production. However, fed-batch systems can be relatively expensive and challenging for ethanol manufacturers to control and manage.

There is a desire to develop methods of propagating organisms such as yeast using batch process protocols instead of fed-batch process protocols because batch processes can be relatively more simple to control and can be more tolerant to variation in process parameters (e.g., with respect to varying levels of a carbon source and the Crabtree effect).

Further, there is a desire to use alternative, more accessible, and/or more economical components used in a propagation medium (e.g., carbon source, nutrient source, and the like).

SUMMARY OF INVENTION

The present invention relates to methods of propagating an organism that use a nutrient source including a stillage component (e.g., thin stillage), preferably derived from a corn-to-ethanol process. Surprisingly, including a stillage component as part of (or all of) a nutrient source of a propagation medium can provide as good as, or better than, results as compared to a conventional nutrient source such as yeast extract. Further, it has been discovered that very low amounts of initial cell mass can be used in propagating an organism such as yeast (e.g., as low as 1.0 gram of yeast per liter of medium, as low as 0.02 grams of yeast per liter of medium, or even lower).

Also, including a stillage component in the nutrient component of a propagation medium permits the use of a by-product from a corn-to-ethanol process in a lignocellulosic ethanol process. This can be especially convenient where the two processes are co-located.

Further, the present invention relates to methods of propagating an organism that use a nutrient source that includes a stillage component (e.g., thin stillage) and a carbon source having xylose. For organisms that can use xylose instead of or in addition to glucose for propagation, using xylose can avoid the Crabtree effect observed with using glucose. For example, the level of xylose can vary over a wide range (e.g., including a level corresponding to level of glucose that would induce the Crabtree effect), yet propagation via aerobic respirative pathway continues without switching to an anaerobic fermentative pathway to produce ethanol to an undue degree. Organisms that can use xylose in this manner include some genetically modified yeast. Advantageously, using xylose can prevent "contaminant" yeast (such as wild type *S. cerevisiae*) from competing with the organism that is targeted for propagation.

Further, because the Crabtree effect can be avoided using xylose, propagation can be performed using a batch process.

Finally, including xylose in the carbon source can advantageously condition the yeast to the environment expected in fermentation, which can help the yeast perform more effectively.

According to one aspect of the present invention, a method of propagating an organism that can convert one or more monosaccharides into a biochemical, the method including:
  providing a first cell mass of the organism;
  providing a carbon source that can support growth of the first cell mass of the organism, wherein the carbon source comprises at least xylose;
  providing a nutrient source that can support growth of the first cell mass of the organism, wherein the nutrient source comprises a stillage component;
  combining at least the carbon source and the nutrient source to form a medium for propagating the organism; and
  combining the first cell mass of the organism with the carbon source and the nutrient source to propagate the first cell mass of the organism for a time period to form a second cell mass of the organism.

According to another aspect of the present invention, a method of propagating an organism that can convert one or more monosaccharides into a biochemical, the method including:
  providing a first cell mass of the organism;
  providing a carbon source that can support growth of the first cell mass of the organism, wherein the carbon source comprises one or more monosaccharides;
  providing a nutrient source that can support growth of the first cell mass of the organism, wherein the nutrient source comprises a stillage component;
  combining at least the carbon source and the nutrient source to form a medium for propagating the organism, wherein the first cell mass is present in an amount less than 1.0 gram of organisms per liter of medium; and
  combining the first cell mass of the organism with the carbon source and the nutrient source to propagate the first cell mass of the organism for a time period to form a second cell mass of the organism.

According to another aspect of the present invention, a composition includes:
  a first cell mass of an organism that can convert one or more monosaccharides into a biochemical, wherein the organism is present in an amount of less than 1.0 gram of organisms per liter of the composition;

xylose in an amount in the range of from 0.1 to 10 percent by weight of the composition; and a stillage component in an amount in the range of from 5 to 35 grams solids per liter of the composition.

In preferred embodiments, the organism includes genetically modified *Saccharomyces cerevisiae*, especially genetically modified *Saccharomyces cerevisiae* that can convert xylose and glucose to ethanol.

BRIEF DESCRIPTION OF THE DRAWINGS

FIGS. 3A and 3B show a table and graph, respectively, of the ethanol produced by a genetically modified strain of *S. cerevisiae* in media containing various levels of xylose supplemented with either yeast extract, peptone or with thin stillage as a nutrient source.

FIGS. 4A and 4B show a table and graph, respectively, of the ethanol produced after fermentation by a genetically modified strain of *S. cerevisiae* in media with 11 percent w/v xylose supplemented with thin stillage at various levels.

DETAILED DESCRIPTION

Figure 1:
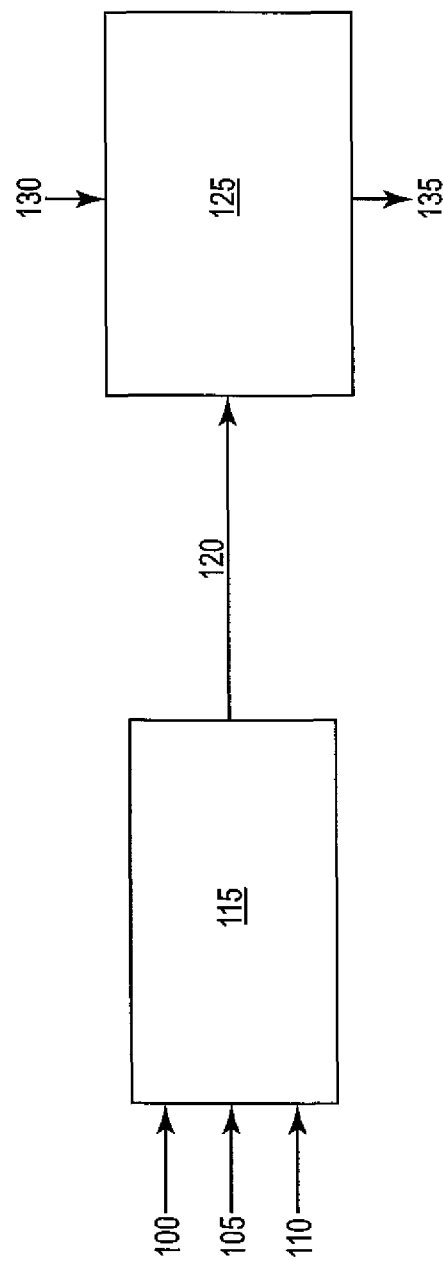
FIG. 1 shows a flow diagram of a propagation system according to the present invention for propagating an organism that can convert one or more monosaccharides into a biochemical.

The present invention relates to propagating an organism that can convert one or more monosaccharides into a biochemical. Propagating such an organism can be useful in many contexts. For example, propagation can be used to reproduce an initial (e.g., "starter") population of the organism so as to generate a larger population of the organism that is sufficient for use in fermentation to make a fermentation product. An exemplary process flow diagram is illustrated in FIG. 1. As shown in FIG. 1, a first cell mass of the organism 100, a carbon source 105, and a nutrient source 110 are combined in a propagation system 115 so that the first cell mass 100 can reproduce and form a second cell mass 120. The second cell mass 120 can then be used in a fermentation system 125 to convert one or more monosaccharides (e.g., from a pretreated lignocellulosic biomass) 130 into a fermentation product 135 that includes a biochemical such as a biofuel (e.g., ethanol, butanol, and the like).

Organisms that can convert one or more monosaccharides into a biochemical are well known and include, e.g., bacteria and/or fungi such as yeast. The product biochemicals can vary depending on the conditions that are provided. In many embodiments, the biochemicals include biofuels such as ethanol, butanol, and the like. In preferred embodiments, the organism includes one or more ethanologenic organisms (i.e., "ethanologens"). As used herein, an "ethanologen" refers to a microorganism that can convert one or more monosaccharides (e.g., glucose, xylose, and the like) into at least ethanol. The ethanologenic organism can be a prokaryotic organism and/or a eukaryotic organism such as *Escherichia coli*, *Klebsiella oxytoca*, *Zymomonas mobilis*, *Clostridium thermocellum*, *Saccharomyces cerevisiae*, and/or *Pichia stipitis*. In preferred embodiments, an ethanologen includes yeast capable of metabolizing at least xylose to ethanol. An example of yeast that can metabolize at least xylose to ethanol includes genetically modified recombinant yeast. In preferred embodiments, such genetically modified yeast includes genetically modified recombinant *Saccharomyces cerevisiae*. According to one embodiment, the ethanologen is a strain of *Saccharomyces cerevisiae* yeast altered to convert (i.e., ferment) xylose and glucose to ethanol (i.e., a genetically modified yeast derived from an organism as described in U.S. Pat. No. 7,622,284).

As used herein, a "carbon source" refers to one or more compounds that include at least one carbon atom and can be used by an organism such as an ethanologen to grow and/or reproduce to create an increased cell mass of the ethanologen. Exemplary carbon sources include monosaccharides such as glucose, fructose, galactose, mannose, xylose, and the like; disaccharides such as lactose, maltose, sucrose, cellobiose and the like; oligosaccharides; polysaccharides such as cellulose, hemicelluloses, starch, xylan and the like; single carbon substrates including only one carbon atom such as methanol; and polyols such as glycerol, but not limited thereto.

In a preferred embodiment, the carbon source includes at least xylose. In some embodiments, the carbon source can include substantially all xylose with little to no glucose. Xylose for use in the present invention can be obtained from many different sources. Preferably, at least a portion of the xylose used in a method of propagating ethanologen according to the present invention includes xylose liquor that is obtained from treating a feedstock such as lignocellulosic feedstock that is to be fermented by the ethanologen to make ethanol. Treating lignocellulosic feedstock in a manner that produces a xylose liquor is well known and is disclosed in, e.g., U.S. Ser. No. 12/717,002 having filing date Mar. 3, 2010; U.S. Pat. No. 5,424,417 (Torget et al.), U.S. Pat. No. 6,022,419 (Torget et al.), wherein the entireties of said documents are incorporated herein by reference for all purposes.

Figure 2:
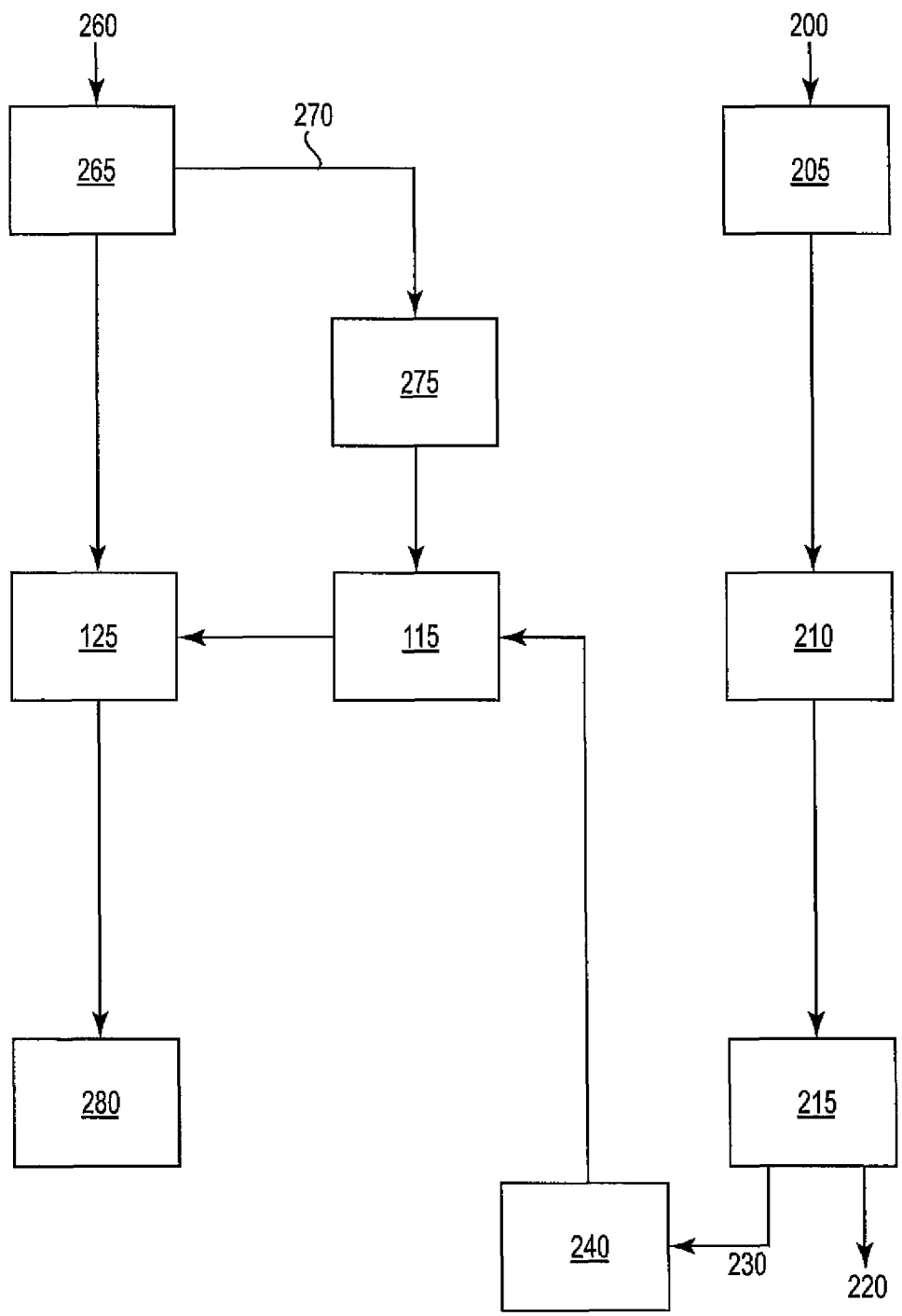
FIG. 2 shows a flow diagram of a propagation system according to the present invention for propagating an organism that can convert one or more monosaccharides into a biochemical in the context of a lignocellulosic ethanol system that is co-located with a corn grain-to-ethanol system.

Treating lignocellulosic feedstock to provide a xylose for use in propagating an organism according to the present invention will be described by reference to FIG. 2. FIG. 2 illustrates a flow diagram of a biorefinery that includes a lignocellulosic ethanol production facility (which produces ethanol from sugars obtained by pretreating lignocellulosic material) co-located with a corn-based ethanol production facility (which produces ethanol from starch contained in corn kernels). Co-locating the two ethanol production facilities can permit certain plant systems to be shared such as, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared by milling (e.g. by fractionation) in the corn-based ethanol production facility, may be supplied to the lignocellulosic ethanol production facility as a feedstock. Fuel or energy sources such as methane or lignin from the lignocellulosic ethanol production facility may be used to supply power to either or both co-located facilities. According to other alternative embodiments, a biorefinery (e.g. a lignocellulosic ethanol production facility) may be co-located with other types of plants and facilities, for example an electric power plant, a waste treatment facility, a lumber mill, a paper plant or a facility that processes agricultural products.

As shown in FIG. 2, a lignocellulosic feedstock 260 is pretreated in system 265 so as to create a xylose liquor 270 that can be used in a propagation system 115 according to the present invention.

Exemplary feedstock 260 includes biomass of all types such as fiber material from one or more of grains and/or one or more lignocellulosic substrates such as hardwoods, grasses, softwood, waste paper and pulp, municipal wastes, agricultural wastes such as straws, corn cobs, corn stover, and mixtures thereof. Lignocellulosic feedstock is well known and includes cellulose, hemicellulose and lignin. In a preferred embodiment, feedstock for producing xylose includes plant material from the corn plant, such as corn cobs, husks and leaves and stalks. For example, the plant material may include (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any other combinations of cobs, husks/leaves and stalks from the corn plant. Typically, corn stalks include the upper half or three-quarters portion of the stalk. According to an alternative embodiment, the lignocellulosic plant material may include fiber from the corn kernel (e.g. in some combination with other plant material). In exemplary embodiments, the lignocellulosic plant material of the biomass (from the corn plant) includes (by weight) cellulose at about 30 to 55 percent, hemicellulose at about 20 to 50 percent, and lignin at about 10 to 25 percent. In some embodiments, the lignocellulosic plant material of the biomass (cobs, husks/leaves and stalk portions from the corn plant) includes (by weight) cellulose at about 35 to 45 percent, hemicellulose at about 24 to 42 percent, and lignin at about 12 to 20 percent.

Pretreatment system 265 can include one or more subsystems for preparing and pretreating the feedstock 260. A biomass preparation sub-system may include an apparatus for receipt/unloading of the biomass, cleaning (i.e. removal of foreign matter), grinding (i.e. milling, reduction or densification) and transport and conveyance for processing at the plant. According to an exemplary embodiment, biomass in the form of corn cobs and stover may be delivered to the biorefinery and stored (e.g. in bales, piles or bins, etc.) and managed for use at the facility. According to other exemplary embodiments, a preparation sub-system of the biorefinery may be configured to prepare any of a wide variety of types of biomass (i.e. plant material) for treatment and processing into ethanol and other bioproducts at the plant. According to a preferred embodiment, biomass includes plant material from the corn plant is prepared and cleaned at a preparation sub-system (not shown).

After preparation, the biomass can be pre-treated according to well known techniques to create C5 and/or C6 sugars. For example, biomass can be mixed with water into a slurry to facilitate the break down (e.g. by hydrolysis) of the biomass into the C5 and/or C6 sugars. In some embodiments, pretreatment system 265 can include adding an acid to the prepared biomass to facilitate the break down of the biomass for separation into a liquid component (C5 stream from which fermentable C5 sugars can be recovered) and a solids component (C6 stream from which fermentable C6 sugars can be accessed).

According to a preferred embodiment, an acid can be applied to the biomass in a reaction vessel under determined operating conditions (i.e. acid concentration, pH, temperature, time, pressure, solids loading, flow rate, supply of process water or steam, etc.) and the biomass can be agitated/mixed in the reaction vessel to facilitate the break down of the biomass. According to exemplary embodiments, an acid such as sulfuric acid, hydrochloric acid, nitric acid, phosphoric acid, acetic acid, etc. (or a formulation/mixture of acids) can be applied to the biomass. According to a particularly preferred embodiment, sulfuric acid is applied to the biomass in pretreatment.

In exemplary embodiments, the liquid component (C5 stream) includes water; dissolved sugars (such as xylose, arabinose and glucose) that can be made available for fermentation into ethanol and/or propagation of an ethanologen; acids and other soluble components recovered from the hemicellulose. According to an exemplary embodiment, the liquid component may comprise approximately 5 to 7 percent solids (i.e. suspended/residual solids such as partially-hydrolyzed hemicellulose, cellulose and lignin). According to a particularly preferred embodiment, the liquid component will include at least 2 to 4 percent xylose (by weight); according to other embodiments, the liquid component will include no less than 1 to 2 percent xylose (by weight). In some embodiments, pretreatment of the biomass can yield a liquid component that includes (by weight) xylose at no less than 1.0 percent and a solids component that comprises (by weight) cellulose (from which glucose can be made available) at no less than 40 percent.

At least a portion of the xylose created in system 265 can be transferred to propagation system 115 via stream 270 and used as a carbon source as described herein to propagate an organism. As shown in FIG. 2, the xylose stream 270 from pretreatment system 265 can optionally be treated in system 275 so as to, e.g., remove and/or recover by-products, such as solids, organic acids, furfural, and/or the like.

In many embodiments, some of the xylose created in system 265 will be transferred to fermentation system 125, along with at least a portion of the C6 sugars created in system 265, and converted into ethanol by the organisms produced in system 115.

Fermentation product from the fermentation system 125 is then supplied to a distillation system 280, where the ethanol is recovered.

Referring to FIG. 1 again, xylose can be provided as part (or all) of carbon source 105 in an amount so as to help reproduce (propagate) a desired population of an organism (e.g., ethanologen) within a desired amount of time. The amount of xylose provided can depend on factors such as the type and amount of other carbon sources present, the type and amount of nutrient source present, pH, temperature, desired time period for propagation, and the like. In some embodiments, the xylose is provided in an amount in the range of from 0.1 to 10 percent by weight of medium, preferably 0.5 to 5 percent by weight of medium (medium is discussed below).

In addition to a carbon source, a nutrient source is also included to help propagate organisms such as ethanologens. As used herein, a "nutrient source" refers to one or more materials that can be used by an organism such as an ethanologen to grow and/or reproduce to create an increased cell mass of the ethanologen. Conventional sources of nutrient sources are well known and include, e.g., yeast extract. Conventional nutrients that can be used for propagation of organisms such as yeast can be commercially obtained under the tradename GO-FERM from Scott Laboratories Ltd, Pickering, ON, Canada.

According to the present invention, the nutrient source includes a stillage component. Stillage is well known and is a byproduct of distilling a fermentation product. For example, a well known process for making stillage is a corn grain-to-ethanol process and will be explained with respect to FIG. 2.

As shown in FIG. 2, grain such as corn, barley, wheat, and/or sorghum 200 is prepared in system 205 so that it can be fermented in system 210 into a fermentation product that includes one or more biochemicals such as ethanol. Either the whole grain can be used or only one or more portions of the grain can be used. For example, system 205 may mill whole grains for fermentation or fractionate the grains into one or more separated portions before milling. Stillage can also be derived from lignocellulosic feedstock that has been fermented and distilled and is referred to herein as "cellulosic whole stillage." Stillage derived at least in part from one or more grain sources such as corn kernels is preferred. After milling, the milled grain material can be further processed to break down polysaccharides and/or oligosaccharides into one or more monosaccharides such as glucose that can be fermented by, e.g., yeast. Methods of breaking down polysaccharides such as starch into glucose are well known and include e.g. hot water, such as hot water that includes an added acid such as sulfuric acid, and/or enzymatic pretreatment. After fermentation 210, the fermentation product is distilled in system 215, where the ethanol 220 is removed from the fermented mash in a distillation column. After the ethanol 220 is removed, the remaining residue is removed as stillage residue 230. The stillage residue 230 is known as "whole stillage." The whole stillage 230 can optionally further processed via one or more systems 240 to refine the whole stillage before being delivered to propagation system 115. For example, the whole stillage 230 can be subjected to a solid-liquid separation process to produce a solid stream of residue, also known as wet cake, and a liquid stream of residue, also referred to as thin stillage. The thin stillage can be further processed to increase the solids concentration by evaporation resulting in condensed distillers solubles or syrup. Also, the thin stillage can be further refined by removing at least a portion of suspended solids from the thin stillage via centrifugation to produce "clarified" thin stillage. It is noted that in many conventional corn ethanol processes, the syrup is mixed back with the separated solid stream or wet cake and fed to a rotary drum dryer to remove the remaining moisture. The resulting dry solids are typically referred to as Dried Distillers Grains and Solubles or "DDGS", and can be sold as animal feed.

However, according to the present invention, such stillage residues from the grain-to-ethanol producing process, including the whole stillage, thin stillage, and/or syrup can form a stillage component to be used as at least part of the nutrient source for propagating organisms such as yeast. Using at least a stillage component provides an alternative or additional nutrient source as compared to, e.g., yeast extract and can take advantage of co-locating grain-to-ethanol and lignocellulosic ethanol processes by using at least a portion of a by-product (whole stillage) from one process as an input for the other process. Applicants have found that using a stillage component can propagate yeast as well as, or even better, than other nutrient sources such as yeast extract.

In some embodiments, the nutrient source includes a stillage component that includes whole stillage, thin stillage, syrup derived from thin stillage, and any combination thereof. Preferably, the stillage component includes syrup derived from thin stillage, thin stillage, or combinations thereof.

The stillage component can be provided in any amount so as to help reproduce (propagate) and generate a desired population of organism (e.g., ethanologen) within a given amount of time. The amount of stillage component provided can depend on factors such as the type and amount of other nutrient sources present, the type and amount of carbon sources present, pH, temperature, desired time period for propagation, and the like. In some embodiments, the nutrient source includes thin stillage derived from whole corn grain in an amount in the range of from 5 to 35 grams solids per liter of the medium (medium is discussed below).

Propagating an organism that can convert one or more monosaccharides into a biochemical according to the present invention will be described below by reference to an ethanologen such as genetically modified yeast for making ethanol from material derived from pretreating lignocellulosic material. However, as explained above, the present invention is not limited to propagating such yeast.

As shown in FIG. 1, propagating an ethanologen includes combining at least the carbon source 105 and the nutrient source 110 to form a medium to facilitate growth of a sufficient amount of ethanologen (i.e. ethanologen cell mass) for inoculation (i.e. ethanologen inoculum to be supplied) to a fermentation system 125. The first cell mass of the organism (e.g., ethanologen) 100 can be included either while the medium is being formed, after the medium is formed, or both.

According to an exemplary embodiment the growth medium for the propagation system 115 includes water, a nutrient source 110 having a stillage component (e.g., thin stillage), a carbon source 105 including xylose, and, optionally, one or more additional agents (not shown).

Optional additional agents for propagating yeast are well known and include, e.g., agents supplied with an ethanologen such as antibiotics, supplemental or accessory enzymes, materials for adjusting and maintaining pH, nutrients or other components providing nutritional or other benefits to the organism. Optional additional nutrients include, e.g., yeast extract, urea, diammonium phosphate, magnesium sulfate, zinc sulfate or other salts, etc.

The ratio of nutrient source to carbon source is selected to grow a desired cell mass of organism such as a sufficient size cell mass of yeast for fermentation in a lignocellulosic ethanol process. Factors in selecting the ratio of nutrient source to carbon source include the type(s) and amount(s) of nutrient sources, the type(s) and amount(s) of carbon sources, types and amounts of additional growth medium agent(s), the types and initial amounts of organisms, the time period targeted for growing the organism, pH, temperature, and the like. Additional considerations include whether it is desired to condition the organisms during propagation to the environment expected during fermentation. Conditioning organisms to the fermentation environment can advantageously help the organisms operate (e.g., convert sugar to ethanol) more effectively.

In exemplary embodiments, the stillage residue comprises thin stillage and the weight ratio of xylose to solids of thin stillage is in the range of from 0.05 to 20, preferably from 0.1 to 10, more preferably from 0.2 to 5, and even more preferably from 0.5 to 2.5.

Propagating the organism can begin when the organism is present in the growth medium and desired conditions are present. Conditions to consider for propagation of an organism such as an ethanologen include, e.g., amount of ingredients, pH, time period for growth of the organism, stir speed (if stirring is present), exposure to oxygen (aeration), temperature, and the like.

In preferred embodiments, the first cell mass (e.g., initial cell mass) of the organism is present in an amount less than 10.0 grams of ethanologens per liter of medium, preferably less than 5.0 grams of ethanologens per liter of medium, and even more preferably less than 0.1 grams of ethanologens per liter of medium.

The cell mass can be propagated, depending on conditions, for a time period to produce a desired cell mass. Typically, the desired cell mass is a size sufficient to ferment sugar into an alcohol (e.g., ethanol) within an economically desirable time period. Exemplary time periods include from 12-48 hours, or even 16-24 hours. In exemplary embodiments, the second (e.g., second or final) cell mass of the ethanologen is present in an amount in the range of from 0.5 to 40 grams of ethanologens per liter of medium within a time period in the range of from 8 to 48 hours, wherein the time period begins when the first cell mass of the ethanologens is combined with the carbon source and the nutrient source to propagate the first cell mass of the ethanologens. Preferably, the desired (e.g., second or final) cell mass of the ethanologen is present in an amount in the range of from 1 to 20 grams of ethanologens per liter of medium within a time period in the range of from 12 to 48 hours, wherein the time period begins when the first cell mass of the ethanologens is combined with the carbon source and the nutrient source to propagate the first cell mass of the ethanologens.

According to embodiments where the organism includes yeast, the propagation system preferably provides for the selective growth of yeast that can use xylose as a carbon source (i.e. yeast that will propagate in a medium that includes xylose) even if other yeast is present (e.g., as a contaminant); in a medium that provides xylose as a sole carbon source (i.e. a medium that does not contain substantial amounts of glucose), yeast that are capable of propagating using xylose as a carbon source will propagate and other/contaminant yeast that may not be as capable of propagating using xylose as a carbon source (such as more common forms of yeast that typically propagate in a medium containing glucose) will not propagate at the same rate (or at all).

The pH of the growth medium can be at a pH that helps reproduce (propagate) and generate a desired population of organism (e.g., ethanologen) within a desired amount of time. In some embodiments, the pH is between 4 and 8, preferably between 5 and 7, and even more preferably between 5 and 6. Techniques for adjusting and maintaining pH of a growth medium for propagating organisms such as an ethanologen are well known and include, e.g., adding one or more acidic materials and/or adding one or more alkaline materials.

The temperature of the growth medium can be at a temperature that helps reproduce (propagate) and generate a desired population of organism (e.g., ethanologen) within a desired amount of time. In some embodiments, the temperature is at a temperature in the range of from 15° C. to 50° C., preferably from 20° C. to 40° C., and even more preferably from 25° C. to 40° C.

Propagation according to the present invention of an organism (e.g., *Saccharomyces cerevisiae*) can be performed according to a continuous process, fed-batch process, a batch process, or combinations thereof. Preferably, batch process as certain benefits associated therewith. In some embodiments such as those that propagate *Saccharomyces cerevisiae*, xylose is provided in an amount as the carbon source such that the well-known "Crabtree effect" is not a concern so a batch process can be performed without producing an undue amount of ethanol. That is, in some embodiments relatively high levels of xylose, unlike glucose, do not cause the propagation process to switch from a respirative pathway to an anaerobic pathway so as to generate ethanol instead of reproducing and increasing the cell mass. A batch process can be highly desirable as it can be relatively easier to manage and control as compared to a continuous or fed-batch process.

In preferred embodiments, the growth medium is aerated and/or agitated (stirred) for at least a portion of the propagation process so as to help provide sufficient oxygen levels throughout the medium so as to promote aerobic respiration and, therefore, reproduction of the organism instead of, e.g., anaerobic fermentation production of ethanol. In some embodiments, if sufficient oxygen is not provided to the propagation medium, the process can switch to an anaerobic pathway and promote fermentation so as to produce alcohol to an undue degree. Preferably, propagation is aerated for the entire duration of propagation. Methods of aerating and stirring are well-known. Exemplary mixing speeds include from 100 to 750 rpms. Exemplary aeration rates include from 0.5 to 1 volumetric units of air per volumetric units of medium per minute (vvm). In some embodiments, the propagation vessel is about 10 times smaller than the fermentation vessel if aeration is not utilized. In some embodiments, the propagation vessel is about 20 to 30 times smaller than the fermentation vessel if aeration is utilized.

According to exemplary embodiments where the organism includes yeast, to grow (inoculate) the yeast in the propagation system the temperature may be maintained in a range of about 28 to 32 degrees Celsius and the pH is in a range of about 5.2 to 5.8 for a time of at least 12 hours. For example, the yeast inoculum can be incubated under conditions including a temperature of about 30 degrees Celsius and a pH of about 5.5 for about 17 hours.

A propagation system according to the present invention can be performed in one or more stages. For example, where yeast is the organism to be propagated, the propagation system can include at least two stages. In a first stage, a yeast culture can be grown into an initial yeast inoculum. In the first propagation stage, the initial yeast inoculum is introduced into a vessel and diluted (e.g. by 250×). In the vessel, the initial yeast inoculum and a portion of the carbon source (e.g., liquid component including xylose and/or other sugars), a portion of the nutrient source (e.g., thin stillage), and water may be supplied along with optional agents (discussed above). According to exemplary embodiments, the temperature may be maintained in a range of about 26 to 37 degrees and the pH in a range of about 3.5 to 6.5 for a time of at least 24 hours. For example, yeast can be grown in the first propagation stage under conditions including a temperature of about 30 degrees Celsius and a pH of about 5.5 for about 24 hours.

In the second propagation stage, the yeast inoculum from the first propagation stage is diluted (e.g. by 10×), typically after being transferred to another vessel. In the vessel, the yeast inoculum from the first propagation stage and a portion of the carbon source (i.e. liquid component including xylose and/or other sugars), a portion of the nutrient source (e.g., thin stillage), and water may be supplied along with optional agents (discussed above). According to exemplary embodiments, the temperature may be maintained in a range of about 26 to 37 degrees and the pH in a range of about 3.5 to 6.5 for a time of at least 24 hours. For example, yeast can be grown in the second propagation stage under conditions comprising a temperature of about 30 degrees Celsius and a pH of about 5.5 for about 24 hours.

According to a particularly preferred embodiment the yeast cell mass will grow by about 200 to 500 fold in the first stage and about 20 to 40 fold in the second stage.

After propagation, cell mass of ethanologen is provided to a fermentation system such as system 125 so as to ferment a biomass such as pretreated lignocellulosic material and produce ethanol.

The present invention will now be further illustrated by reference to the Examples below.

Example 1

Figure 3B:
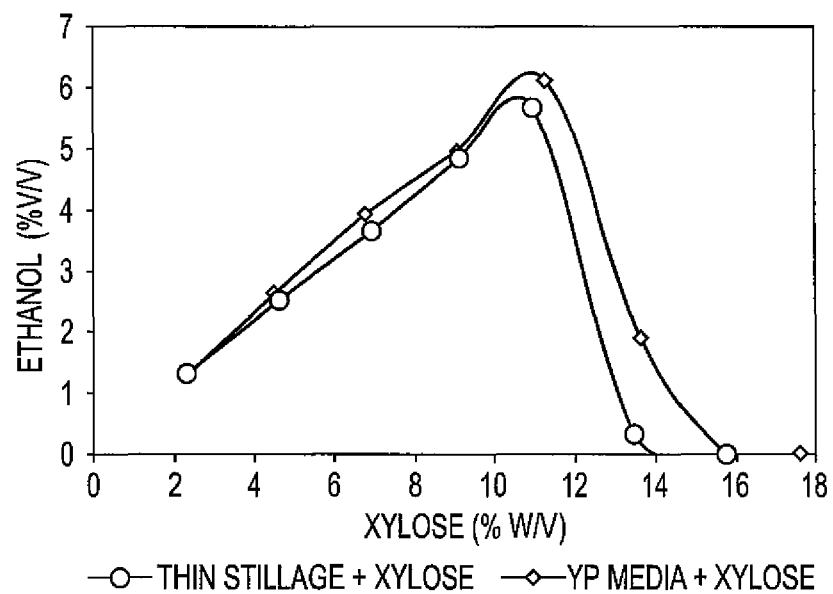

A yeast growth and fermentation system was used in this example to evaluate the effect of thin stillage as a nutrient source instead of yeast extract. This example measured the ethanol produced by a genetically modified strain of *S. cerevisiae* in media containing various levels of xylose supplemented with either yeast extract, peptone or with thin stillage as nutrient source. The ethanologen was genetically modified yeast (strain no. RN1016 obtained from DSM, Heerlen, Netherlands). The experiment was conducted in 125 mL Erlenmeyer flasks. Each flask contained 50 mL of an experimental media: sterile Yeast extract, Peptone (YP) media or thin stillage media. Thin stillage used was collected from a BPX™ process dry grind corn ethanol biorefinery located in Scotland, S. Dak. Various amounts of a 50 percent w/w solution of xylose was added to the sterile YP media (yeast extract and peptone, each at 10 g/L final concentration), to achieve the concentrations of xylose as observed. Additionally, various amounts of the 50 percent w/w xylose solution was added to a different set of flasks containing thin stillage to achieve the concentrations xylose as observed. After xylose was added to the reactors, the pH of each reactor was adjusted to 5.5. To prevent bacterial contamination, Lactoside247, an antimicrobial product commercially available from Lallemand Ethanol Technology of Milwaukee, Wis., was added to the reactors for a final concentration of 8 ppm. Urea was added at 62.5 mg/L (~1.04 mM) to the reactors containing thin stillage. The media in the flasks was inoculated at 0.5-0.6 g (dry yeast) from the prepared culture per Liter and the flasks were incubated at 32 degrees Celsius in a water bath shaker, operating at an approximate rate of 150 rpm. Samples were withdrawn periodically and analyzed for sugars, organic acids & ethanol composition using high pressure liquid chromatography (HPLC). The data from Example 1 is shown in the table in FIG. 3A and the graph shown in FIG. 3B.

Example 2

Figure 4B:
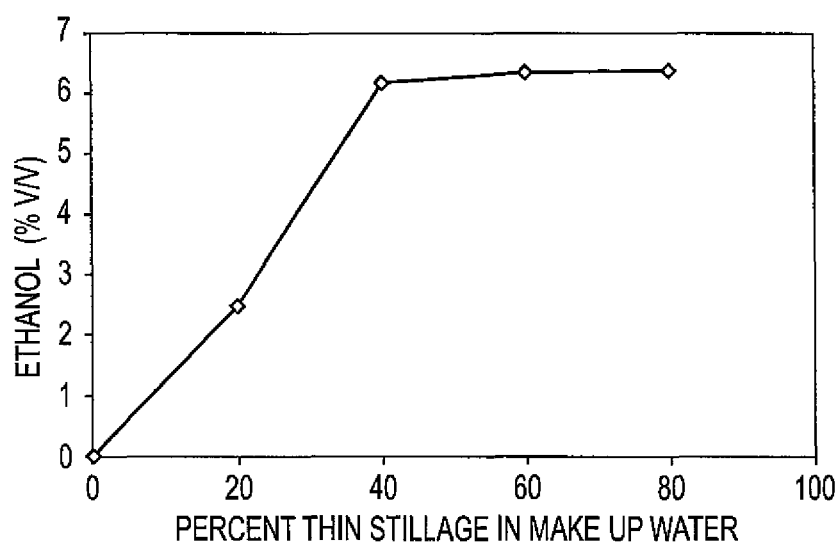

In Example 2, the optimum level of thin stillage was identified. This example measured the ethanol produced after fermentation by a genetically modified strain of *S. cerevisiae* and residual xylose in media with 11 percent w/v xylose supplemented with thin stillage at various levels. The values are averages of duplicate fermentations. The ethanologen was genetically modified yeast (strain no. RN1016 obtained from DSM, Heerlen, Netherlands). Xylose was kept constant at about 11 percent w/v and the level of thin stillage was varied—0 percent, 20 percent, 40 percent, 60 percent and 80 percent. The pH of the media in the flasks was adjusted to 5.5 after xylose was combined with makeup water in 125 mL Erlenmeyer flasks. The antimicrobial Lactoside247 and Urea were added to the flasks at 8 ppm and 62.5 mg/L, respectively. Media in the flasks was inoculated at 0.5-0.6 g (dry yeast) from the prepared culture per Liter and the flasks were incubated at 32 degrees Celsius in a water bath shaker at a rate of approximately 150 rpm. Samples were withdrawn periodically and analyzed for sugars, organic acids & ethanol composition using HPLC. The data from Example 2 is shown in the table in FIG. 4A and the graph shown in FIG. 4B.

Example 3

Figure 5A:
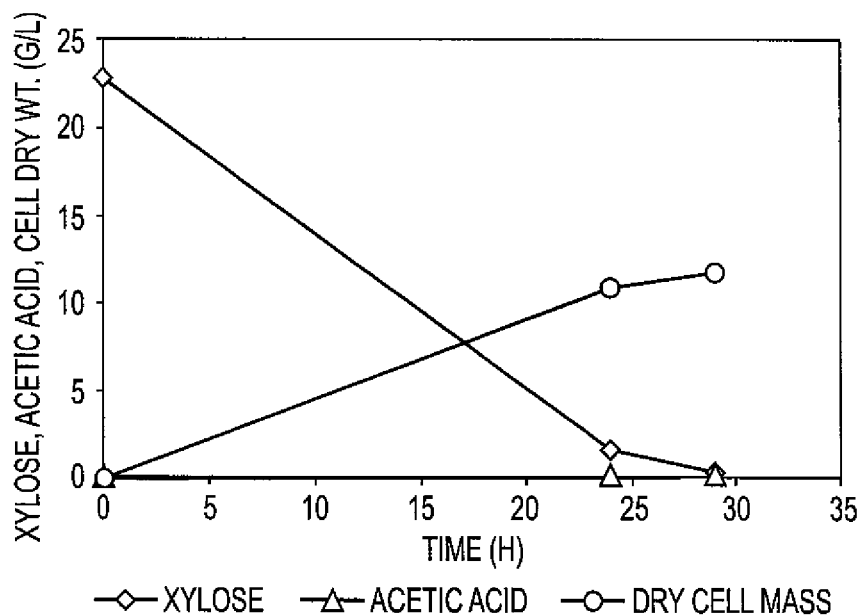
FIG. 5A shows a graph illustrating cell growth of a genetically modified strain of *S. cerevisiae* using pure xylose as the carbon source and thin stillage from a corn-ethanol biorefinery as a nutrient source.
Figure 5B:
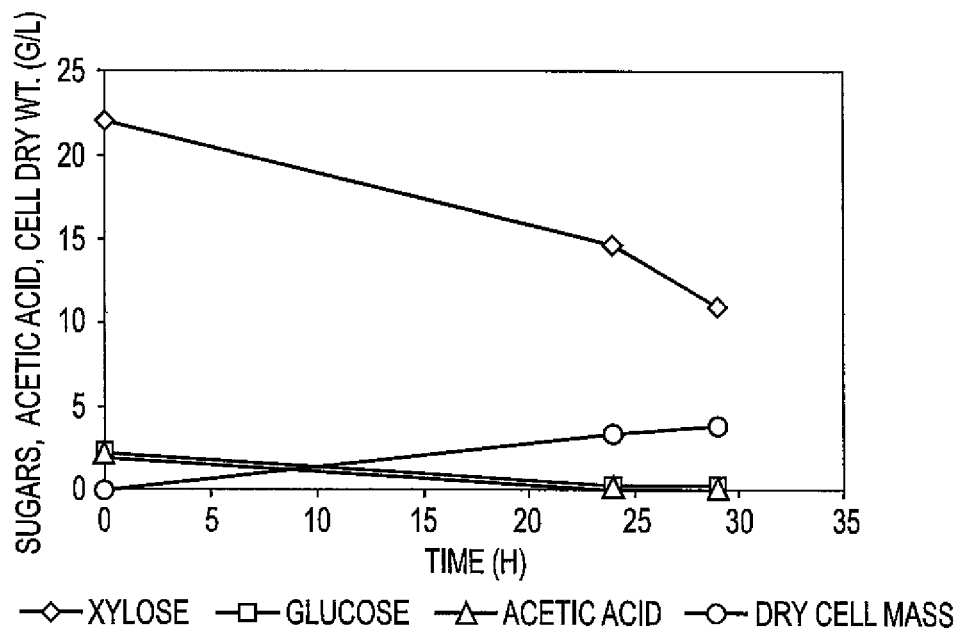
FIG. 5B shows a the graph illustrating cell growth of a genetically modified strain of *S. cerevisiae* using xylose liquor from dilute acid pretreatment of lignocellulosic biomass as the carbon source and thin stillage from a corn-ethanol biorefinery as a nutrient source.

Yeast propagation system was used in this example to show the media used for propagation of genetically modified yeast capable of metabolizing C5 sugars such as xylose. The ethanologen was genetically modified yeast (strain no. RN1016 obtained from DSM, Heerlen, Netherlands). The yeast culture was grown in YP (12.5 g/L yeast extract & 10 g/L peptone) medium supplemented with 2% w/v glucose and 1% w/v xylose at 30° C. overnight. After 17 h, the culture was transferred to 1500 mL of yeast propagation media (Approx. at 15 g dry solids/L of thin stillage from corn-ethanol biorefinery, pure xylose or xylose liquor from dilute acid pretreatment of lignocellulosic biomass diluted to 2% w/v xylose, and 0.24 g/L urea) in a Bioflo310 reactor at a rate of 0.02 g (dry yeast)/L. Urea is not required if the pH of the propagation medium is adjusted with ammonium hydroxide. The yeast was aerobically propagated using the standard propagation protocol (initial pH of 5.5; agitation, 450 rpm; aeration, 0.5 vvm; temperature, 31.1° C.) for 24 h. The contents of the propagator are then transferred to the fermentor. The data from Example 3 is shown in the graph in FIG. 5A for pure xylose as the carbon source and the graph shown in FIG. 5B for xylose liquor from dilute acid pretreatment of lignocellulosic biomass as the carbon source.

What is claimed is:

1. A method of propagating an organism that can convert one or more monosaccharides into a biochemical, the method comprising:
    providing a first cell mass of the organism;
    providing a carbon source that can support growth of the first cell mass of the organism, wherein the carbon source comprises xylose;
    providing a nutrient source that can support growth of the first cell mass of the organism, wherein the nutrient source comprises a stillage component and, wherein the stillage component comprises thin stillage that is a by-product of fermenting a grain material;
    combining at least the carbon source and the nutrient source to form a medium for propagating the organism, wherein the weight ratio of xylose to solids of thin stillage is in the range of from 0.5 to 2.5; and
    combining the first cell mass of the organism with the carbon source and the nutrient source to propagate the first cell mass of the organism for a time period to form a second cell mass of the organism.

2. The method of claim 1, wherein the organism comprises one or more ethanologens.

3. The method of claim 2, wherein the first cell mass is present in an amount less than 1.0 gram of ethanologens per liter of medium.

4. The method of claim 2, wherein the first cell mass is present in an amount less than 0.1 grams of ethanologens per liter of medium.

5. The method of claim 4, wherein the second cell mass of the ethanologens is present in an amount in the range of from 1 to 20 grams of ethanologens per liter of medium within a time period in the range of from 12 to 48 hours, wherein the time period begins when the first cell mass of the ethanologens is combined with the carbon source and the nutrient source to propagate the first cell mass of the ethanologens.

6. The method of claim 2, wherein the one or more ethanologens comprise yeast capable of metabolizing at least xylose to ethanol.

7. The method of claim 6 wherein the yeast comprises genetically modified yeast capable of metabolizing at least xylose to ethanol.

8. The method of claim 7, wherein the genetically modified yeast comprises genetically modified *Saccharomyces cerevisiae*.

9. The method of claim 1, wherein the grain material comprises at least a portion of whole corn kernel material.

10. The method of claim 1, wherein the thin stillage is provided in an amount in the range of from 5 to 35 grams solids per liter of the medium.

11. The method of claim 1, wherein the xylose is provided in an amount in the range of from 0.1 to 10 percent by weight of medium.

12. The method of claim 1, wherein the first cell mass of the organism is combined with the carbon source and the nutrient source to propagate the first cell mass of the organism to form a second cell mass of the organism according to a batch process.

13. The method of claim 1, wherein the carbon source comprises xylose liquor that is a by-product of pretreating lignocellulosic substrate with at least water.

14. The method of claim 13, wherein the pretreated lignocellulosic substrate is derived from corn cobs, corn stover, or combinations thereof.

15. The method of claim 1, wherein the organism is exposed to aerobic conditions during at least a portion of the time period.

16. A method of propagating an organism that can convert one or more monosaccharides into a biochemical, the method comprising:
    providing a first cell mass of the organism;
    providing a carbon source that can support growth of the first cell mass of the organism, wherein the carbon source comprises xylose;
    providing a nutrient source that can support growth of the first cell mass of the organism, wherein the nutrient source comprises a stillage component and, wherein the stillage component comprises thin stillage that is a by-product of fermenting a grain material;
    combining at least the carbon source and the nutrient source to form a medium for propagating the organism, wherein the first cell mass is present in an amount less than 1.0 gram of organisms per liter of medium and wherein the weight ratio of xylose to solids of thin stillage is in the range of from 0.5 to 2.5; and
    combining the first cell mass of the organism with the carbon source and the nutrient source to propagate the first cell mass of the organism for a time period to form a second cell mass of the organism.

17. The method of claim 16, wherein the organism comprises genetically modified *Saccharomyces cerevisiae*.

18. A system of propagating an organism that can convert one or more monosaccharides into a biochemical, the system comprising:
    a propagation vessel, comprising a composition comprising:
    a carbon source that can support growth of the first cell mass of the organism, wherein the carbon source comprises xylose;
    a nutrient source that can support growth of the first cell mass of the organism, wherein the nutrient source comprises a stillage component and, wherein the stillage component comprises thin stillage that is a by-product of fermenting a grain material;
    wherein the stillage component comprises thin stillage and the weight ratio of xylose to solids of thin stillage is in the range of from 0.5 to 2.5; and
    a first cell mass of the organism, wherein the first cell mass of the organism can use the xylose and thin stillage to propagate the first cell mass of the organism for a time period to form a second cell mass of the organism; and
    an aerator coupled to the propagation vessel to aerate the composition.

* * * * *